United States Patent
Ouali et al.

(10) Patent No.: US 9,498,411 B2
(45) Date of Patent: Nov. 22, 2016

(54) MICROCAPSULES AND USES THEREOF

(71) Applicant: FIRMENICH SA, Geneva (CH)

(72) Inventors: Lahoussine Ouali, Vetraz-Monthhoux (FR); Marlène Jacquemond, Viuz-en-Sallaz (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/295,276

(22) Filed: Jun. 3, 2014

(65) Prior Publication Data

US 2014/0287978 A1    Sep. 25, 2014

Related U.S. Application Data

(62) Division of application No. 13/130,224, filed as application No. PCT/IB2009/055811 on Dec. 17, 2009, now Pat. No. 8,778,867.

(30) Foreign Application Priority Data

Dec. 18, 2008    (EP) ..................... 08172188

(51) Int. Cl.
| | | |
|---|---|---|
| A61K 8/11 | (2006.01) |
| A61Q 13/00 | (2006.01) |
| C11D 3/50 | (2006.01) |
| A61K 8/84 | (2006.01) |
| A61K 8/87 | (2006.01) |
| A61Q 5/02 | (2006.01) |
| B01J 13/16 | (2006.01) |
| C11D 3/00 | (2006.01) |

(Continued)

(52) U.S. Cl.
CPC . *A61K 8/11* (2013.01); *A61K 8/84* (2013.01); *A61K 8/87* (2013.01); *A61Q 5/02* (2013.01); *A61Q 13/00* (2013.01); *B01J 13/16* (2013.01); *C11D 3/0015* (2013.01); *C11D 3/3726* (2013.01); *C11D 3/505* (2013.01); *C11D 17/0039* (2013.01); *A61K 2800/412* (2013.01); *A61K 2800/5426* (2013.01); *A61K 2800/56* (2013.01)

(58) Field of Classification Search
None
See application file for complete search history.

(56) References Cited

U.S. PATENT DOCUMENTS 3,594,328 A * 7/1971 Schibler ............... B01J 13/02
                                                  264/4
3,730,905 A * 5/1973 Koerner et al. .... B01F 17/0071
                                                  264/4

(Continued)

FOREIGN PATENT DOCUMENTS

| EP | 1 407 754 A1 | 4/2004 |
| EP | 1 693 104 A1 | 8/2006 |

(Continued)

OTHER PUBLICATIONS

Hanson et al., "Nanoscale double emulsions stabilized by single-component block copolypeptides," Nature, 455:85-89 (2008).

(Continued)

*Primary Examiner* — Jeffrey Washville
(74) *Attorney, Agent, or Firm* — Winston & Strawn LLP

(57) ABSTRACT

The present invention relates to perfume-containing microcapsules having both an aqueous inner phase and an oily inner phase, which can be used in home or personal care products, as well as to the process for producing these microcapsules and the consumer products comprising them.

19 Claims, 5 Drawing Sheets

(51) Int. Cl.
*C11D 17/00* (2006.01)
*C11D 3/37* (2006.01)

(56) References Cited

U.S. PATENT DOCUMENTS

| | | | |
|---|---|---|---|
| 4,083,798 A | 4/1978 | Versteeg | |
| 4,891,172 A * | 1/1990 | Matsushita et al. | 264/4.33 |
| 5,354,742 A | 10/1994 | Deming et al. | |
| 2002/0136773 A1* | 9/2002 | Scher et al. | 424/497 |
| 2004/0241485 A1 | 12/2004 | Kleban et al. | |
| 2005/0089540 A1* | 4/2005 | Uchiyama et al. | 424/401 |
| 2007/0065379 A1* | 3/2007 | Biatry et al. | 424/59 |
| 2007/0202063 A1 | 8/2007 | Dihora et al. | |
| 2008/0317795 A1* | 12/2008 | Traynor et al. | 424/401 |

FOREIGN PATENT DOCUMENTS

| | | |
|---|---|---|
| EP | 1 741 775 B1 | 1/2007 |
| GB | 2 432 843 A | 6/2007 |
| GB | 2 432 850 A | 6/2007 |
| GB | 2 432 851 A | 6/2007 |
| GB | 2 432 852 A | 6/2007 |
| WO | 02/060573 A2 | 8/2002 |
| WO | 2004/041251 A1 | 5/2004 |
| WO | 2004/098767 A1 | 11/2004 |
| WO | 2005/054422 A1 | 6/2005 |
| WO | 2007/004166 A1 | 1/2007 |
| WO | 2007/062733 A1 | 6/2007 |
| WO | 2007/062833 A1 | 6/2007 |
| WO | 2008/016684 A1 | 2/2008 |

OTHER PUBLICATIONS

Kiyoyama et al., "Preparation of Cross-Linked Microcapsules Entrapping Inorganic Salt by In-situ Polymerization in (W/O/W) Emulsion System," Journal of Chemical Engineering of Japan, 34(1):36-42 (2001).

International Search Report and Written Opinion, Appl. No. PCT/IB2009/055811, Jul. 26, 2010.

* cited by examiner

MICROCAPSULES AND USES THEREOF

CROSS-REFERENCE TO RELATED APPLICATIONS

This application is a division of U.S. application Ser. No. 13/130,224 filed May 19, 2011, which is the U.S. national stage of International application no. PCT/IB2009/055811 filed Dec. 17, 2009, which claims priority to European application no. 08172188.8 filed Dec. 18, 2008, the entire content of each of which is incorporated herein by reference thereto.

TECHNICAL FIELD

The present invention relates to a process for producing perfume-containing microcapsules having both an aqueous inner phase and an oily inner phase, which can be used in home or personal care products, as well as to the process for producing these microcapsules and the consumer products comprising them.

PRIOR ART

One of the problems faced by the perfumery industry lies in the relatively rapid loss of the olfactive benefit provided by odoriferous compounds due to their volatility, particularly that of "top-notes". This problem is generally tackled using a delivery system, e.g. capsules containing a perfume, to release the fragrance in a controlled manner.

Several capsules comprising a multiple core are known form the prior art. Nevertheless these capsules are very different from the ones of the present invention.

For example, WO 2004/041251 describes multicore capsules having three shells of which at least one comprises a coacervate complex. Such capsules have a membrane that is rich in water and less tightly cross-linked than the polyurea or polyurethane walls of the capsules of the present invention. As a consequence, perfumes are not sufficiently well retained by this type of capsules. Moreover, the described coacervated capsules would not be sufficiently stable in several types of bases commonly used in the field of functional perfumery.

S. Kiyoyama et al., Journal of Chemical Engineering of Japan, vol. 34 (1) (2001), pp. 36-42 describes cross-linked microcapsules prepared by in-situ copolymerization of styrene and divinyl benzene in a water-in-oil-in-water emulsion system. Capsules having walls formed of this type of monomers cannot bear any cationic charges and are therefore not as well dispersed in the perfumery base in which they are used and not as well deposited on the surface on which they are applied, as the cationic polyurea or polyurethane capsules of the invention.

U.S. Pat. No. 4,083,798 describes compositions prepared by dispersing an aqueous phase into an oil phase to form a first emulsion. This first emulsion is then dispersed as droplets in a second aqueous phase, in the presence of a water soluble protein and a gelling polysaccharide. This type of capsule wall is not as tightly cross-linked as the polyurea or polyurethane walls of the invention's capsules and therefore they are much less efficient in retaining perfumes.

J. A. Hanson et al., Nature, vol. 455 (2008), pp. 85-87, describes water-in-oil-in-water emulsions stabilized using a single-component, synthetic amphiphilic diblock copolypeptide surfactant.

WO 02/060573 describes a capsule-in-capsule system consisting of an external capsule with an external capsule envelope and internal capsules located therein. Both internal and external capsules can have very diverse types of walls including polyurea or polyurethane walls. However, the disclosed capsules are not cationic.

To summarize, none of the prior known multicore capsules are at the same time polyurea or polyurethane based and cationic. Other prior art documents describe polyurea or polyurethane capsules, some of them being cationic, but none have the same advantageous characteristics as the invention's capsules. In particular none of the prior known cationic polyurea and polyurethane capsules has a multiple core capable of encapsulating both hydrophilic and hydrophobic ingredients. The prior art never suggests multicore cationic polyurea or polyurethane microcapsules or the advantageous properties of such capsules. In particular, multicore polyurea or polyurethane microcapsules bearing permanent cationic charges covalently linked to the capsule wall are not disclosed or suggested.

The problem of the present invention is that of providing cationic multicore microcapsules capable of encapsulating both hydrophilic and hydrophobic materials. The capsules of the invention solve this problem. Indeed, they have a tightly cross-linked polyurea or polyurethane wall which is very efficient in retaining perfuming ingredients. They further have the advantage of bearing permanent cationic charges with a high charge density and therefore of having an improved deposition on the surface on which they are applied and a better dispersion in consumer product bases. Moreover, the permanent cationic charges are present on compounds which are covalently linked to the microcapsule wall and which therefore remain stable on the capsule wall even in the presence of anionic compounds in the medium in which they are used.

SUMMARY OF THE INVENTION

The present invention relates to cationic polyurea or polyurethane microcapsules having an aqueous inner phase and an oily inner phase. The invention also concerns the process for preparing these capsules, as well as perfuming compositions and perfumed articles containing them.

DETAILED DESCRIPTION OF THE INVENTION

One object of the present invention is a microcapsule comprising:

a) a core consisting of at least one aqueous phase dispersed in a continuous oily phase, wherein
   i. the aqueous phase is surrounded by a layer formed of the reaction product of at least one polyisocyanate with at least one organic compound comprising a permanent quaternary ammonium group and a primary amine or hydroxyl group;
   ii. the continuous oily phase comprises a perfuming ingredient or composition; and
b) a shell surrounding said core and formed of the reaction product of at least one polyisocyanate with
   i. at least one organic compound comprising a permanent quaternary ammonium group and a primary amine or hydroxyl group; and
   ii. a polyamine or a polyol.

According to one embodiment of the invention, the aqueous phase is surrounded by a layer formed of the reaction product of at least one polyisocyanate with at least one organic compound comprising a permanent quaternary ammonium group and a primary amine or hydroxyl group and with a polyamine or a polyol.

In one embodiment of the invention, the polyisocyanate is reacted not only with the organic compound comprising a permanent quaternary ammonium group and a primary amine or hydroxyl group, but also with a polyamine or a polyol, as defined below. In such case, the layer is formed of the reaction product of at least one polyisocyanate with at least one organic compound comprising a permanent quaternary ammonium group and a primary amine or hydroxyl group and with a polyamine or a polyol.

Figure 1:
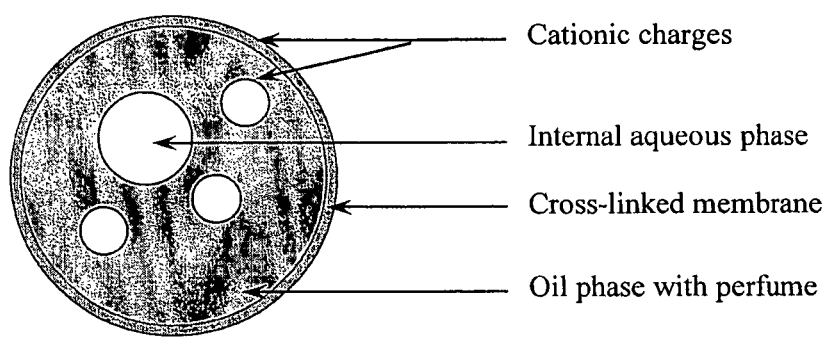
FIG. 1 represents schematically the structure of the microcapsules of the invention.

FIG. 1 is a schematic representation of the microcapsules of the invention when the layer surrounding the inner aqueous phase is formed of the reaction product of at least one polyisocyanate with at least one organic compound comprising a permanent quaternary ammonium group and a primary amine or hydroxyl group.

In the case where the layer surrounding the aqueous phase is formed of the reaction product of the polyisocyanate with the organic compound and with a polyamine or polyol, the general structure of the microcapsule is the same, but the layer surrounding the inner aqueous phase is crosslinked in the same way as the external wall of the capsule.

The aqueous phase comprises water and optionally other water miscible solvents, preferably together with a hydrophilic active. Such hydrophilic active is for example a perfume, a colorant, an antimicrobial or antifungal agent or any other additive of current use in perfuming compositions, provided that it is soluble in water. Preferably such hydrophilic active is a perfume. The hydrophilic active is preferably characterized by a log P value below 2. The log P value of a compound can easily be determined, for example by calculation using the EPI suite v3.10, 2000, U.S. Environmental Protection Agency.

For the purpose of the present invention, "perfume" means a single perfuming ingredient or a mixture of ingredients, in the form of a perfuming composition. By "perfuming ingredients" it is understood here compounds which are used as active ingredients in perfuming preparations or compositions in order to impart a hedonic effect when applied to a surface. In other words, such compounds, to be considered as being perfuming ones, must be recognized by a person skilled in the art of perfumery as being able to impart or modify in a positive or pleasant way the odor of a composition or of an article or surface, and not just as having an odor. Moreover, this definition is also meant to include compounds that do not necessarily have an odor but are capable of modulating the odor of a perfuming composition, perfumed article or surface and, as a result, of modifying the perception by a user of the odor of such a composition, article or surface.

Specific examples of such perfuming ingredients can be found in the current literature, for example in Perfume and Flavour Chemicals, 1969 (and later editions), by S. Arctander, Montclair N.J. (USA), as well as in the vast patent and other literature related to the perfume industry. They are well known to the person skilled in the art of perfuming consumer products, that is, of imparting a pleasant odour to a consumer product.

The aqueous phase can also advantageously comprise hydrophilic inorganic particles such as silica particles or titanium oxide, in order to adjust the density of the microcapsules. By so doing, the density of the microcapsules can be brought to a value similar to that of the end product into which it is intended to incorporate them and therefore the capsules are maintained homogeneously suspended and dispersed in such liquid products. This is particularly advantageous in perfuming microcapsules because the specific gravity of the perfuming ingredients is usually lower than 1 g/ml.

Any polyisocyanate compound is suitable for reacting with the organic compound and optionally with the polyamine or polyol, but a polyisocyanate comprising at least two isocyanate groups or at least three isocyanate groups is preferred. Low volatility polyisocyanate molecules are preferred because of their low toxicity. In particular, the polyisocyanate can advantageously be selected from the group consisting of a trimer of hexamethylene diisocyanate, a trimer of isophorone diisocyanate or a Biuret of hexamethylene diisocyanate, among which a Biuret of hexamethylene diisocyanate is even more preferred.

The organic compound which is reacted with the polyisocyanate (referred to herein as "organic compound") can be a monomer, an oligomer or a polymer, provided that it comprises at least one permanent quaternary ammonium group and at least one primary amine or hydroxyl group. By a permanent quaternary ammonium group, we mean here a quaternary ammonium group which is always present, and in particular, which is present independently of the pH. This definition excludes amine groups which are protonated only at acidic pH. The organic compound therefore bears a permanent cationic charge.

Particular examples of suitable compounds for reacting with the polyisocyanate are 2-hydrazino-N,N,N-trimethyl-2-oxoethanammonium chloride (Girard reagent T from Acros Organics), the amino acids lysine and arginine, quaternized triethanolamine, 2-aminoethyl-trimethylammonium chloride hydrochloride and 2-hydroxyethyl-trimethylammonium hydroxide, among which 2-hydrazino-N,N,N-trimethyl-2-oxoethanammonium chloride, quaternized triethanolamine and 2-aminoethyl-trimethylammonium chloride hydrochloride are particularly appreciated. The amino acids lysine and arginine are also particularly useful because they are natural compounds.

The amount of polyisocyanate in the microcapsules of the invention is typically comprised between 2 and 20% by weight, relative to the total weight of the microcapsule, whereas the amount of cationic organic compound is typically of from 0.2 to 5% by weight, these percentages being relative to the total weight of the microcapsules.

The continuous oily phase comprises a hydrophobic active. Such hydrophobic active is for example a perfume, a colorant, an antimicrobial or antifungal agent or any additive of current use in perfuming compositions. Preferably such hydrophobic active is a perfume. The hydrophobic active is preferably characterized by a log P value above 2. The perfume is as defined above.

The perfume may be dissolved in a solvent of current use in the perfume industry. The solvent is preferably not an alcohol. Examples of such solvents are diethyl phthalate, isopropyl myristate, Abalyn™ (origin: Eastman), benzyl benzoate, ethyl citrate, limonene or other terpenes, or isoparaffins. Preferably, the solvent is very hydrophobic and highly sterically hindered, like for example Abalyn™. The continuous phase may additionally contain as optional ingredients any other types of hydrophobic actives and additives commonly used in the field of perfumery.

The total amount of active, and preferably of perfume, in the capsules of the invention is typically comprised between 25 and 60% by weight, preferably between 30 and 60% by weight, more preferably between 40 and 60% by weight, relative to the total weight of the microcapsules. This amount includes all actives, and preferably all the perfume, contained in the core (i.e. in the oily phase as well as in the aqueous phase).

The core is encapsulated in a crosslinked polyurea or polyurethane wall formed by reaction of a polyamine or polyol with at least one polyisocyanate and with at least one cationic organic compound as described above. An interfacial polymerisation of the polyamine or polyol with the cationic emulsifier obtained by reacting the polyisocyanate with the cationic organic compound, as well as with the free polyisocyanate molecules which are dissolved in the oily phase, takes place. Firstly, the reaction occurs between the polyamine or polyol and the emulsifier, which forms a layer surrounding the core, thus achieving the cross-linking of the wall. The polyamine or polyol also reacts with free polyisocyanate molecules which are present near the border of the oily phase. This double reaction provides a wall bearing cationic charges on the external side and being sufficiently broad to retain the oily phase efficiently.

A polyurea microcapsule wall is formed when a polyamine is used. Particularly efficient polyamines are water soluble guanidine salts and guanidine. By "water soluble guanidine salt" it is meant a salt soluble in water and resulting from the reaction of guanidine with an acid. One example of such salts is guanidine carbonate.

In the case where a polyol is used as the cross-linker, a polyurethane microcapsule wall is formed. As polyol, glycerol is preferred.

The use of specific proportions of polyisocyanate versus polyamine or polyol is advantageous. Therefore, preferably, for each mole of isocyanate group, 1 to 10, preferably 2 to 5 moles of amine or alcohol groups are present. Accordingly there is added an excess of the cross-linking agent.

The specific composition of the polyurea or polyurethane wall is key in obtaining microcapsules that are at the fine balance between release and retention so as to achieve satisfactory slow and constant release of fragrances over time, once the capsules are placed on textiles, skin or hair, while showing the desired stability of the perfume retention in the product base (e.g. counteracts efficiently the extraction of the perfume by the surfactants of the consumer product). The selection of the polyamine or polyol and of the polyisocyanate, among the ones mentioned above, enables the fine tuning of the properties and stability of the capsules.

Upon their formation using the process described below, the capsules are dispersed in a continuous outer aqueous phase. However the capsules of the invention can also be provided in an isolated or dried form, in which case there does not remain any outer aqueous phase.

The microcapsules of the invention are preferably characterized by a mean diameter comprised between 5 and 100 μm, preferably between 5 to 50 μm. In the present context, "mean diameter" refers to the arithmetic mean. With microcapsules of this size, optimal deposition and/or adherence of microcapsules to the targeted surface, e.g. textile, hair or skin, is obtained.

These capsules are also preferably characterized by a zeta potential comprised between 40 and 80 mV, preferably between 60 and 80 mV. A suitable apparatus for measuring the zeta potential is Zetasizer Nano ZS (Malvern Instruments).

Due to the presence of permanent cationic charges at the surface of the capsules, the zeta potential does not change with the pH. Moreover, since the cationic charges are covalently linked, the cationic compounds are not removed even in the present of anionic compounds such as anionic surfactants that may be encountered in several consumer product bases. The zeta potential therefore remains stable in all types of conditions.

The microcapsules of the invention can be prepared by a process comprising the following steps a) reacting at least one polyisocyanate with at least one organic compound comprising a permanent quaternary ammonium group and a primary amine or hydroxyl group in water or in an aqueous solution of a hydrophilic active, so as to form an emulsion of an aqueous phase in the product obtained by such reaction, the aqueous phase being formed of water or of the aqueous solution of a hydrophilic active;

b) adding an oily phase comprising a perfume and optionally a polyamine or a polyol to the emulsion obtained in step a); and c) adding water to the emulsion obtained in step b) and optionally adding a polyamine or a polyol, if such a polyamine or polyol has not yet been added in step b) such as to form a microcapsule.

In step a) the isocyanate groups react with the primary amine or alcohol groups, but they also react with water molecules and thereby are transformed to amine groups that can react with isocyanates. This reaction induces a cross-linking in the oil phase but its rate remains slower than the rate of reaction between the isocyanate and the primary amine or alcohol. The reaction can also be carried out when the organic coumpound contains more than one reacting group. The product resulting from the reaction of step a) has the structure of a tenside bearing permanent cationic charges and acts as en emulsifier. It is therefore referred to herein as "the emulsifier".

An emulsion takes place, with droplets of aqueous phase dispersed in a continuous phase formed of the emulsifier obtained by the above-described reaction. When the reaction is carried out in an aqueous solution of hydrophilic actives, such actives remain in the aqueous phase of the emulsion.

The reaction of the polyisocyanate with the cationic organic compound is typically carried out at a temperature comprised between 20 and 70° C.

In step b), the oily phase comprising a hydrophobic active, as described above, is admixed with the emulsion obtained in step a). A new emulsion is formed, wherein the aqueous phase formed in step a) is dispersed in the oily phase. A layer of the emulsifier formed in step a) is formed at the interface of the aqueous and oily phases.

In one embodiment of the invention, a polyamine or a polyol is added in step b) together with the oily phase, so that the polyamine of polyol reaches the membrane surrounding the aqueous phase droplets thereby ensuring optimal cross-linking of this internal membrane.

The addition of water in step c) results in the formation of droplets of oily phase dispersed in water, which forms a continuous phase. The aqueous phase droplets surrounded by the emulsifier, as obtained in step b), remain dispersed in the oily phase, so that such aqueous phase droplets are dispersed in the newly formed oily phase droplets. A layer of the emulsifier obtained in step a) is formed at the newly formed interface between water and the dispersed droplets of oily phase. The emulsifier at the interface of the oily phase and water is cross-linked by the effect of the polyamine or polyol, so as to form the outer capsule wall. The cross-linking of the outer wall is achieved in the same way when the polyamine or polyol is added in step b) or in step c).

In a preferred embodiment of the invention, the polyamine or polyol is not added in step b), but in step c).

To achieve optimal cross-linking, for each mole of isocyanate group used in step a), 1 to 10, preferably 2 to 5 moles of amine or alcohol groups are preferably added in step b) or c).

The crosslinking of the polyurea or polyurethane wall is usually performed at temperatures ranging from 20 to 85° C. Preferably the reaction is maintained for 2 to 15 hours, more preferably for 4 to 10 hours. The reaction between the polyisocyanate and the polyol involves the use of a catalyst such as 1,4-diazabicyclo[2,2,2]octane.

In the case of a polyurethane wall, the cross-linking step can be carried out either in basic, neutral or acidic medium, whereas the cross-linking of the polyurea wall is carried out at a pH above 9.

The definition and the concentration of each component used in the process of the invention are as described above in the part of the description related to the capsules themselves.

The process of the invention may further comprise the step of forming a powder with microcapsules using methods commonly known in the art, as for example spray drying.

The process of the invention has the advantage of being carried out in the absence of polyvinyl alcohol. Polyvinyl alcohol is used in many emulsification processes leading to polyurea and polyurethane microcapsules. Nevertheless, it causes strong phase separation in some liquid detergent formulations. Therefore, due to the fact that they are free of polyvinylalcohol, the microcapsules of the invention do not phase separate when incorporated in liquid detergent bases.

The microcapsules of the invention can be advantageously used for the controlled release of the encapsulated perfume. It is therefore particularly appreciated to include these microcapsules as perfuming ingredients in a perfuming composition or in perfumed consumer products.

Therefore, another object of the present invention is a perfuming composition comprising:
a) as perfuming ingredient, a microcapsule of the invention, as defined above;
b) at least one ingredient selected from the group consisting of a perfumery carrier and a perfumery base; and
c) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

Generally speaking, by "perfumery base" we mean here a composition comprising at least one perfuming co-ingredient together with the capsules of the invention.

The "perfuming co-ingredients" can be any perfuming ingredient, as defined above.

Generally speaking, by "perfumery adjuvant" we mean here an ingredient capable of imparting an added benefit such as a color, a particular light resistance, chemical stability, etc. A detailed description of the nature and type of adjuvants commonly used in perfuming bases cannot be exhaustive, but such ingredients are well known to a person skilled in the art.

A composition consisting of microcapsules as defined above and at least one perfumery carrier, represents a particular embodiment of the invention. Another embodiment of the invention is one such perfuming composition further comprising at least one perfumery base, and optionally at least one perfumery adjuvant.

Furthermore, microcapsules as defined above or a perfuming composition comprising such microcapsules, are useful perfuming ingredients, which can be advantageously used in all the fields of modern perfumery, such as fine perfumery or functional perfumery. Indeed, the microcapsules and the perfumes containing them may be advantageously employed in fine or functional perfumery to achieve a more controlled deposition, and consequent release, of perfuming ingredients.

The microcapsules of the invention and the perfuming compositions containing them can be used in various types of perfumed consumer products. This result is highly surprising since said consumer products may contain high amounts (typically more than 10% of their own weight) of specific types of surfactant/tensioactive/solvents and which are known to significantly diminish the stability and the performance of said capsules. In other words, the use of the invention's microcapsules in the consumer products provides unexpected advantages over the same use of prior art capsules.

The microcapsules of the invention provide improved deposition of the perfume on the treated surface together with an improved stability in a chemically aggressive environment and thus a good retention of the perfume, especially in detergents and fabric softeners. The cationic polyurea microcapsules are also well dispersed in the consumer product bases, so that no phase separation is induced upon addition of the capsules to the base and during a sufficient storage period. The microcapsules of the invention provide a controlled release of the encapsulated perfume, said perfume being slowly released from the microcapsules, thus considerably improving the perfume long-lastingness and intensity.

Consequently, a perfumed article comprising:
a) as perfuming ingredient, a microcapsule as defined above or a perfuming composition as defined above; and
b) a consumer product base;
is also an object of the present invention.

For the sake of clarity, it has to be mentioned that, by "consumer product base" we mean here a consumer product which is compatible with perfuming ingredients. In other words, the consumer product base comprises the functional formulation, as well as optionally additional benefit agents, corresponding to a consumer product. The microcapsules of the invention are incorporated to the consumer product base in an olfactively effective amount.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric conditioners, heavy duty cleaners, as well as any other product commonly used in perfumery, namely perfumes, colognes or after-shave lotions, perfumed soaps, shower or bath salts, mousses, creams, oils or gels, hygiene products or hair care products such as shampoos, body-care products, deodorants or antiperspirants, air fresheners and also cosmetic preparations. As detergents it is intended to include here applications such as detergent compositions or cleaning products for washing up, cleaning or treating various surfaces, e.g. intended for textile, dish or hard-surface treatment, whether they are intended for domestic or industrial use. Other perfumed articles are fabric conditioners, ironing waters, papers, wipes or bleaches.

Preferred perfumed articles are powder and liquid detergents, fabric conditioners and hair care products such as shampoos.

The proportions in which the microcapsules of the invention can be incorporated into the various aforementioned articles or compositions vary within a wide range of values. These values are dependent on the nature of the article or product into which they are to be incorporated and on the desired olfactory effect, as well as the nature of the co-ingredients in a given composition, when the microcapsules are mixed with perfuming co-ingredients, solvents or additives commonly used in the art.

For example, typical concentrations of the capsules of the invention in a perfuming composition such as described above may vary within a wide range of values comprised between 1% and 40% by weight, preferably between 5% and 20% by weight, relative to the weight of the perfuming composition. Concentrations lower than these, such as in the order of 0.001% to 5%, more preferably 0.3 to 2%, or even 0.5 to 1%, by weight, relative to the total weight of the consumer product, can be used when these compounds are applied directly in the perfuming of the various consumer products mentioned hereinabove.

Formulations of consumer product bases in which the microcapsules of the invention can be incorporated can be found in the abundant literature relative to such products. These formulations do not warrant a detailed description here, which would in any case not be exhaustive. The person skilled in the art of formulating such consumer products is perfectly able to select the suitable components on the basis of his general knowledge and of the available literature. In particular, examples of such formulations can be found in the patents and patent applications relative to such products, for example in WO 2008/016684 (pages 10 to 14), in US 2007/0202063 (paragraphs [0044] to [0099]), in WO 2007/062833 (pages 26 to 44), in WO 2007/062733 (pages 22 to 40), in WO 2005/054422 (pages 4 to 9), in EP 1741775, in GB 2432843, in GB 2432850, in GB 2432851 or in GB 2432852.

Another object of the present invention is a method for intensifying or prolonging the diffusion effect of the characteristic fragrance of a perfume on a surface, characterized in that said surface is treated with a) a microcapsule of the invention, as defined above, containing said perfume;
b) a perfuming composition of the invention, as defined above, comprising the microcapsule of a); or
c) a perfumed article of the invention, as defined above, comprising the microcapsule of a);

under conditions which are susceptible of allowing the release of the perfuming ingredient.

Suitable surfaces for such treatment are in particular textiles, hard surfaces, hair and skin.

Is also encompassed by the present invention a method for prolonging the effect of a perfume intended for application on a surface, said process comprising:

a) reacting at least one polyisocyanate with at least one organic compound comprising a permanent quaternary ammonium group and a primary amine or hydroxyl group in water or in an aqueous solution of a hydrophilic active, so as to form an emulsion of an aqueous phase in the product obtained by such reaction, the aqueous phase being formed of water or of the aqueous solution of a hydrophilic active;
b) adding an oily phase comprising a perfume and optionally a polyamine or a polyol to the emulsion obtained in step a);
c) adding water to the emulsion obtained in step b) and optionally adding a polyamine or a polyol, if such a polyamine or polyol has not yet been added in step b), so as to form a microcapsule; and
d) applying the microcapsule obtained in step c) to the surface.

The capsules of the invention and the process to prepare them will be further illustrated in the examples below.

EXAMPLES

Example 1

Preparation of Microcapsules According to the Invention

A perfuming composition intended to be encapsulated was prepared by admixing the following ingredients, in the amounts indicated.

TABLE 1

| perfuming composition | |
| --- | --- |
| Ingredients | Parts by weight (%) |
| Hexyl salicylate | 20 |
| Romascone ®[1] | 20 |
| Lilial ®[2] | 20 |
| Lorysia ®[3] | 20 |
| Verdox ®[4] | 20 |

[1] Methyl 2,2-dimethyl-6-methylene-1-cyclohexanecarboxylate, origin: Firmenich SA, Geneva, Switzerland
[2] 3-(4-Tert-butylphenyl)-2-methylpropanal, origin: Givaudan SA, Vernier, Switzerland
[3] 4-(1,1-Dimethylethyl)-1-cyclohexyl acetate, origin: Firmenich SA, Geneva, Switzerland
[4] 2-tert-butyl-1-cyclohexyl acetate, origin: International Flavors and Fragrances, USA The microcapsules of the invention were then prepared by the following process.

a) An amount of 1.55 g of Girard Reagent T (2-hydrazino-N,N,N-trimethyl-2-oxoethanammonium chloride, origin: Acros Organics) was dissolved in 1.07 g of water containing traces of fluorescin. This solution was mixed with 3.33 g of Desmodur® N100 (solvent-free aliphatic polyisocyanate resin based on hexamethylene diisocyanate, origin: Bayer) using an Ultra Turax at 24000 rpm for 2 minutes. The resulting solution was kept at room temperature under magnetic stirring for 2 hours.

b) The reaction mixture was then dispersed in 30.0 g of the perfume described in Table 1 containing traces of Nile Red using an Ultra Turax at 24000 rpm for 3 minutes.

c) An aqueous solution of guanidine carbonate was then prepared by dissolving 2.64 g of guanidine carbonate (origin: Fluka) in 6.06 g of water. The obtained solution was gradually added to the reaction mixture obtained in step b). The system was then maintained at 70° C. for 3 hours under mechanical stirring of 500 rpm.

The obtained capsules were then characterized. A mean particle size of 10 μm was measured by laser diffraction measurements (MasterSizer, Malvern Instruments Ltd). A zeta potential of 65.9±0.6 mV was measured with a Zetasizer Nano ZS (Malvern Instruments Ltd). This high value indicates a high density of the cationic charges at the surface of the microcapsules.

Example 2

Preparation of Microcapsules According to the Invention a) An amount of 1.46 g of Girard Reagent T (2-hydrazino-N,N,N-trimethyl-2-oxoethanammonium chloride, origin: Acros Organics) was dissolved in 2.02 g of water containing traces of fluorescin. This solution was mixed with 6.75 g of Desmodur® N100 (solvent-free aliphatic polyisocyanate resin based on hexamethylene diisocyanate, origin: Bayer) using an Ultra Turax at 24000 rpm for 2 minutes. The resulting solution was kept at room temperature under magnetic stirring for 2 hours.

b) The reaction mixture was then dispersed in 30.1 g of the perfume described in Table 1 containing traces of DABCO (1,4-diazabicyclo [2.2.2]octane, origin: Fluka) and of Nile Red using an Ultra Turax at 24000 rpm for 5 minutes.

c) The system was then stirred continuously with vortex stirrer at 400 rpm. An aqueous solution of glycerol (origin: Fluka) was then prepared by dissolving 2.73 g of guanidine carbonate in 5.41 g of water. The obtained solution was then added in two portions to the reaction mixture obtained in step b). The system was then maintained at 70° C. for 21 hours under mechanical stirring of 500 rpm.

The obtained capsules were then characterized. A mean particle size of 18 μm was measured by laser diffraction measurements (MasterSizer, Malvern Instruments Ltd). A zeta potential of 73.3±5.0 mV was measured with a Zetasizer Nano ZS (Malvern Instruments). This high value indicates a high density of the cationic groups at the surface of the microcapsules.

Example 3

Preparation of Microcapsules According to the Invention a) An amount of 0.75 g of Girard Reagent T (2-hydrazino-N,N,N-trimethyl-2-oxoethanammonium chloride, origin: Acros Organics) was dissolved in 1.07 g of water containing traces of fluorescin. This solution was mixed with 3.33 g of Desmodur® N100 (solvent-free aliphatic polyisocyanate resin based on hexamethylene diisocyanate, origin: Bayer) using an Ultra Turax at 21500 rpm for 2 minutes. The resulting solution was kept at room temperature under magnetic stirring for 2 hours.

b) The reaction mixture was then dispersed in 15.1 g of the perfume described in Table 1 containing traces of Nile Red using an Ultra Turax at 21500 rpm for 2 minutes.

c) An aqueous solution of guanidine carbonate was then prepared by dissolving 0.6 g of guanidine carbonate (origin: Fluka) in 2.77 g of water. The obtained solution was gradually added to the reaction mixture obtained in step b). The system was then maintained at 70° C. for 3 hours under mechanical stirring of 500 rpm.

The obtained capsules were then characterized. A mean particle size of 12 μm was measured by laser diffraction measurements (MasterSizer, Malvern Instruments Ltd). A zeta potential of 64.8±0.4 mV was measured with a Zetasizer Nano ZS (Malvern Instruments). This high value indicates a high density of the cationic groups at the surface of the microcapsules.

Example 4

Preparation of Microcapsules According to the Invention a) An amount of 0.85 g of quaternized triethanolamine (origin: Fluka) was mixed into a solution with 3.5 g of Desmodur® N100 (solvent-free aliphatic polyisocyanate resin based on hexamethylene diisocyanate, origin: Bayer), 3.0 g of the perfume described in Table 1 and traces of DABCO (1,4-diazabicyclo [2.2.2]octane, origin: Fluka). This mixture was dispersed using an Ultra Turax at 24000 rpm for 1 minute and the resulting solution was kept at room temperature under magnetic stirring for 15 minutes.

b) The reaction mixture was then dispersed in 12 g of the perfume described in Table 1 using an Ultra Turax at 24000 rpm for 1 minute.

c) We added slowly 27 g of water into the mixture and we dispersed it using an Ultra Turax at 24000 rpm for 5 minutes.

d) An aqueous solution of guanidine carbonate was then prepared by dissolving 1.0 g of guanidine carbonate (origin: Fluka) in 3.0 g of water. The obtained solution was gradually added to the reaction mixture obtained in step c). The system was then maintained at 70° C. for 16 hours under mechanical stirring of 500 rpm.

Example 5

Preparation of Microcapsules According to the Invention a) An amount of 0.43 g of 2-aminoethyl-trimethylammonium chloride hydrochloride (origin: Fluka) was dissolved in 0.25 g of water then the pH was adjusted to about 11 by using a 30% sodium hydroxide solution. The resulting solution was mixed with 1.79 g of Desmodur® N100 (solvent-free aliphatic polyisocyanate resin based on hexamethylene diisocyanate, origin: Bayer). The entire mixture was maintained under magnetic stirring at room temperature for 7 minutes.

b) The reaction mixture was then dispersed in 7.56 g of the perfume described in Table 1 using an Ultra Turrax at 24000 rpm for 1 minute. An amount of water of 13.18 g was then added in this dispersion, which was then mixed using an Ultra Turrax at 24000 rpm for 5 minutes.

c) An aqueous solution of guanidine carbonate was then prepared by dissolving 0.68 g of guanidine carbonate (origin: Fluka) in 1.66 g of water. The obtained solution was gradually added to the reaction mixture obtained in step b). The system was then maintained at 70° C. for 4 hours under mechanical stirring at 600 rpm.

The obtained capsules were then characterized. A mean particle size of 7 μm was measured by laser diffraction measurements (MasterSizer, Malvern Instruments Ltd). A zeta potential of 46.3±0.2 mV was measured with a Zetasizer Nano ZS (Malvern Instruments). This high value indicates a high density of the cationic groups at the surface of the microcapsules.

Example 6

Determination of the Capsules Structure

Figure 2:
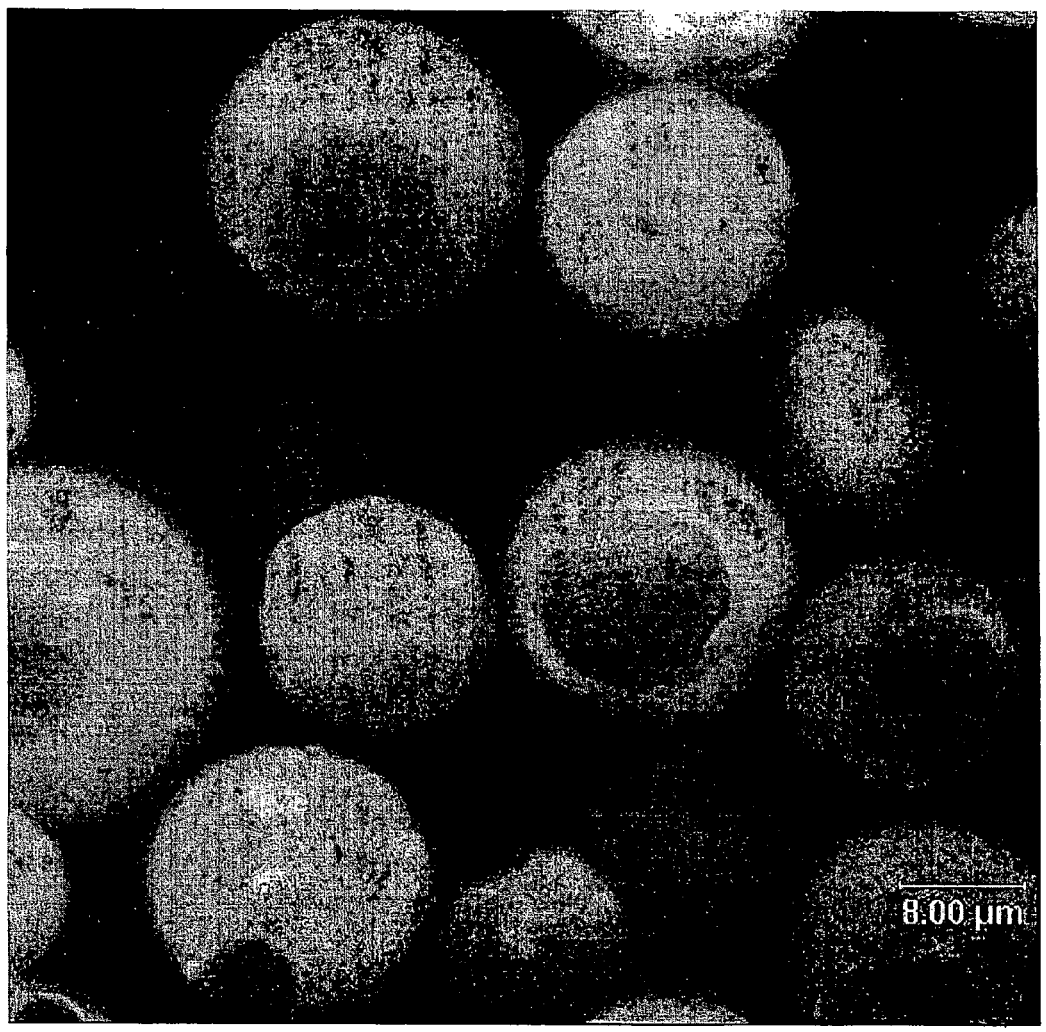
FIG. 2 shows a confocal laser scanning microscopy (CLSM) image of the microcapsules of the invention as obtained by transmittance and fluorescence imaging. The inner oily phase is represented in light grey, whereas the inner aqueous phase is in dark grey, surrounded by the light grey area.

The structure of the capsules was determined by confocal laser scanning microscopy (CLSM). This technique allowed the observation of microcapsules and the analysis of the composition of the internal phase, due to the addition of traces of Nile Red to the perfume and of fluorescin to the water at the beginning of the above described process. FIG. 2 represents the CLSM image of the capsules of Example 3. The perfume phase is represented in light grey, due to the fluorescence of the Nile Red, the inner aqueous phase is represented in dark grey due to the fluorescence of fluorescin, and the external aqueous phase is represented in black (no fluorescence). The multicore structure of the capsules is evident, since in several capsules, an inner aqueous phase (in dark grey) is surrounded by an inner perfume (oily) phase (in light grey).

Figure 3:
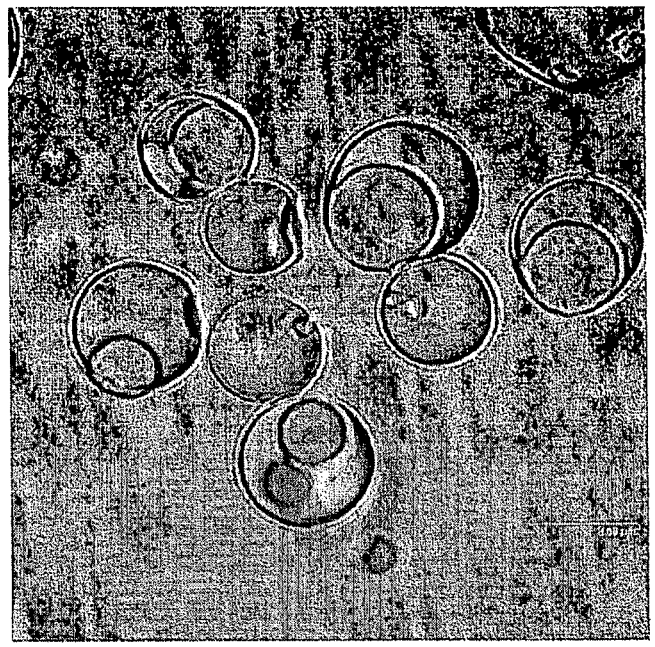
FIGS. 3A and 3B show CLSM images of certain capsules of the invention with very good dispersions observed.
Figure 3B:
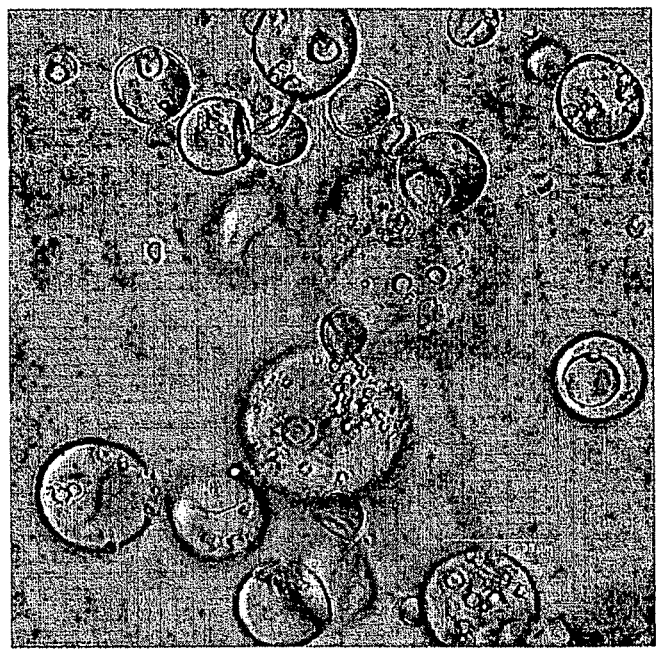

FIGS. 3a and 3b are other representations of the capsules of Example 3, obtained by the CLSM method but without using fluorescence. FIG. 3a) represents the CLSM image of the microcapsules of Example 1, while FIG. 3b) represents the microcapsules of Example 2. Again, these figures show that most of the capsules formed have a multicore structure.

Example 7

Liquid Detergent Comprising the Microcapsules of the Invention and Stability of the Microcapsules The microcapsules of Example 1 were mixed at 0.75% into the commercially available unperfumed Tide® 2× HE Free of perfume & dye (trademark of Procter and Gamble, USA) concentrated liquid detergent. These products were then stored at 38° C. for three weeks.

Figure 4:
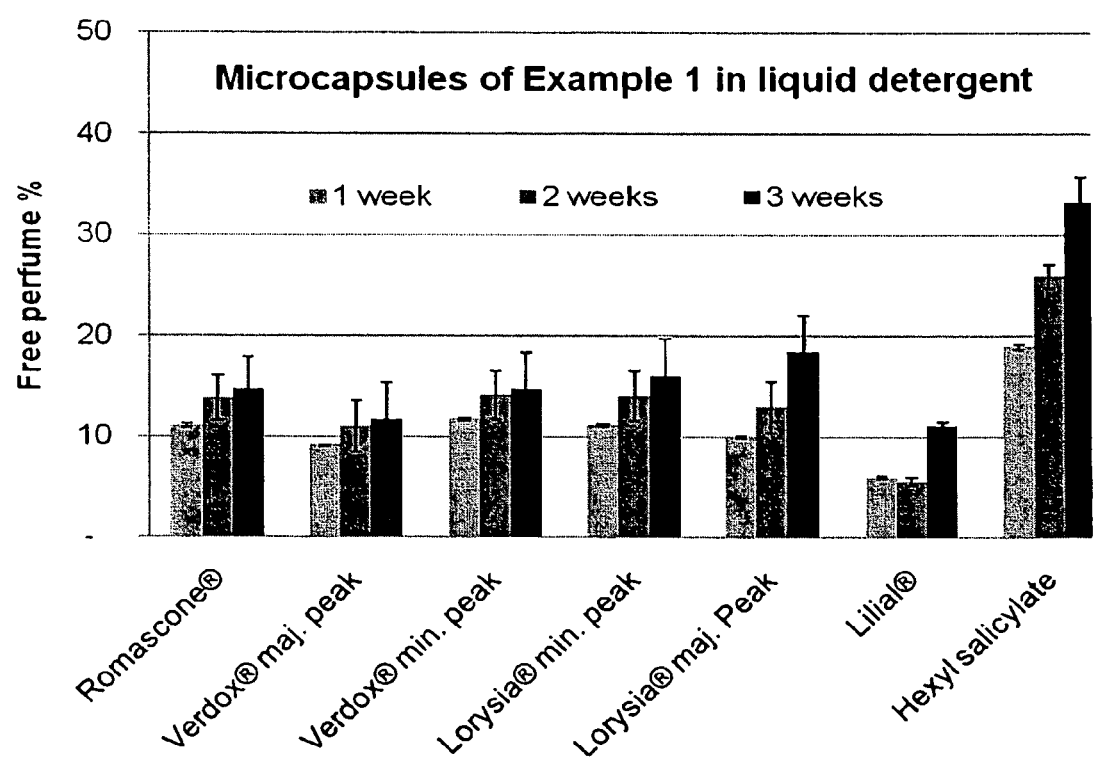
FIG. 4 shows the stability of the perfume retention in the capsules of the invention, when used in a commercial liquid detergent base.

The free perfume was analysed every week. The results are shown in FIG. 4. After three weeks of storage, the amount of free perfume for each ingredient did not exceed 20%, except for hexyl salicylate. These percentages were only slightly higher than those determined after one and two weeks. This indicates a good stability of the perfume retention in the microcapsules in liquid detergent.

Example 8

Fabric Softener Comprising the Microcapsules of the Invention and Stability of the Microcapsules A fabric softener base was prepared by admixing the following ingredients, in the amounts indicated.

TABLE 2

| Formulation of the concentrated fabric softener base | |
|---|---|
| Ingredient | % |
| Stepantex VL90 A Diester Quat[1] | 16.50 |
| Proxel GXL[2] | 0.04 |
| CaCl$_2$ (10% aqueous solution) | 0.20 |
| Water | 83.26 |

[1]Origin: Stepan
[2]Origin: Avecia

The microcapsules suspension of Example 1 was mixed at 1.25% into the unperfumed softener base prepared above. These products were then stored at 38° C. for three weeks.

Figure 5:
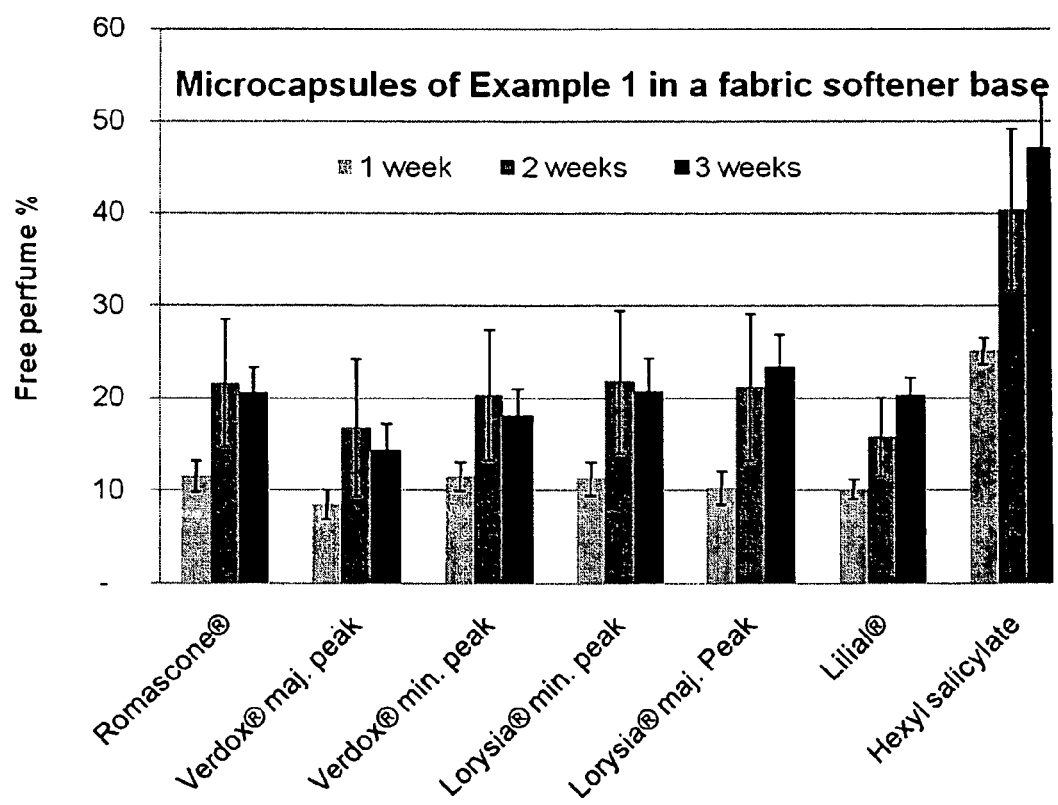
FIG. 5 shows the stability of the perfume retention in the capsules of the invention when used in a fabric softener base.

The free perfume was analysed every week. The results are shown in FIG. 5. After three weeks of storage, the amount of free perfume only slightly exceeded 20%, except for hexyl salicylate. These percentages were only slightly higher than those determined after one and two weeks. This indicates a good stability of the perfume retention in the microcapsules in the fabric softener base.

The rate of perfume partitioning between the microcapsules and the fabric softener base is comparable to the one observed in the liquid detergent (see Example 7).

What is claimed is:

1. A microcapsule comprising:
    a) a core having at least one aqueous phase that is surrounded by a tenside layer and that is dispersed in a continuous oily phase wherein:
        i. the tenside layer is formed of the reaction product consisting of the reaction of at least one polyisocyanate with at least one organic compound having a permanent quaternary ammonium group and a primary amine or hydroxyl group;
        ii. the continuous oily phase surrounds the tenside layer and comprises a perfuming ingredient or composition; and
    b) a shell surrounding said continuous oily phase of the core and formed of the reaction product of the same at least polyisocyanate with
        i. the same at least one organic compound having the permanent quaternary ammonium group and primary amine or hydroxyl group; and
        ii. a polyamine or a polyol;
    wherein the tenside layer and the shell are structurally different and have permanent cationic charges that are imparted to the microcapsule.

2. A microcapsule according to claim 1, wherein the aqueous phase further comprises a perfuming ingredient or other hydrophilic active ingredients.

3. A microcapsule according claim 1, wherein the at least one aqueous phase further comprises silica or other hydrophilic inorganic particles.

4. A microcapsule according to claim 1, wherein the organic compound comprising a permanent quaternary ammonium group and a primary amine group or hydroxyl group is selected from the group consisting of 2-hydrazino-n,n,n-trimethyl-2-oxoethanammonium chloride, lysine, arginine, quaternized triethanolamine, 2-aminoethyl-trimethylammonium chloride hydrochloride and 2 hydroxyethyl-trimethylammonium hydroxide.

5. A microcapsule according to claim 4, wherein the organic compound having a permanent quaternary ammonium group and a primary amine or hydroxyl group is selected from the group consisting of 2 hydrazino-n,n,n- trimethyl-2-oxoethanammonium chloride, quaternized triethanolamine and 2 aminoethyl-trimethylammonium chloride hydrochloride.

6. A microcapsule according to claim 1, wherein the polyamine is guanidine, guanidine carbonate or another water-soluble guanidine salt.

7. A microcapsule according to claim 1, wherein the polyol is glycerol.

8. A microcapsule according to claim 1, which is free of polyvinyl alcohol.

9. A microcapsule according to claim 1, which has a zeta potential comprised between 40 and 80 my.

10. A microcapsule according to claim 1, wherein the perfume content is comprised between 25 and 60% by weight, relative to the total weight of the microcapsule.

11. A process for the preparation of a microcapsule according to claim 1, which comprises:
   a) reacting at least one polyisocyanate only with at least one organic compound having a permanent quaternary ammonium group and a primary amine or hydroxyl group, in water or in an aqueous solution of a hydrophilic active, so as to form an emulsion of an aqueous phase in the product obtained by such reaction, the aqueous phase being formed of water or of the aqueous solution of a hydrophilic active;
   b) adding an oily phase comprising a perfume and optionally a polyamine or a polyol to the emulsion obtained in a); and
   c) adding water to the emulsion obtained in b) and optionally adding a polyamine or a polyol, if such a polyamine or polyol has not yet been added in b) such as to form the outer shell of the microcapsule.

12. A perfuming composition which comprises:
   a) as perfuming ingredient, a microcapsule as defined in claim 1;
   b) at least one ingredient selected from the group consisting of a perfumery carrier and a perfumery base; and
   c) optionally at least one perfumery adjuvant.

13. A consumer article, which comprises:
   a) as perfuming ingredient, a microcapsule as defined in claim 1; and
   b) a consumer product base.

14. A consumer article, which comprises:
   a) as perfuming ingredient, a perfuming composition according to claim 12; and
   b) a consumer product base.

15. The microcapsules of claim 1 which are free of polyvinyl alcohol and have a zeta potential of between 40 and 80 my.

16. A microcapsule comprising:
   a) a core having at least one inner aqueous phase that is surrounded by a tenside layer and that is dispersed in a continuous oily phase wherein:
      i. the tenside layer is formed of the reaction product consisting of at least one polyisocyanate with at least one organic compound having a permanent quaternary ammonium group and a primary amine or hydroxyl group;
      ii. the continuous oily phase surrounds the tenside layer and comprises a volatile perfuming ingredient or composition that provides a perfume content of between 25 and 60% by weight, relative to the total weight of the microcapsule; and
   b) an outer shell surrounding said continuous oily phase of the core and formed of the reaction product of the same at least one polyisocyanate with
      i. the same at least one organic compound having the permanent quaternary ammonium group and primary amine or hydroxyl group; and
      ii. glycerol, guanidine, guanidine carbonate or another water-soluble guanidine salt;
      wherein the tenside layer and the shell are structurally different and have permanent cationic charges that are imparted to the microcapsule and the microcapsule has a zeta potential of between 40 and 80 my;
      wherein the organic compound comprising a permanent quaternary ammonium group and a primary amine or hydroxyl group is selected from the group consisting of 2 hydrazino-n,n,n-trimethyl-2-oxoethanammonium chloride, quaternized triethanolamine and 2 aminoethyl-trimethylammonium chloride hydrochloride.

17. A perfuming composition which comprises:
   a) as perfuming ingredient, a microcapsule as defined in claim 16;
   b) at least one ingredient selected from the group consisting of a perfumery carrier and a perfumery base; and
   c) optionally at least one perfumery adjuvant.

18. A consumer article, which comprises:
   a) as perfuming ingredient, a microcapsule as defined in claim 16; and
   b) a consumer product base.

19. A consumer article, which comprises:
   a) as perfuming ingredient, a perfuming composition according to claim 17; and
   b) a consumer product base.

* * * * *

UNITED STATES PATENT AND TRADEMARK OFFICE
CERTIFICATE OF CORRECTION

| | | |
|---|---|---|
| PATENT NO. | : 9,498,411 B2 | Page 1 of 1 |
| APPLICATION NO. | : 14/295276 | |
| DATED | : November 22, 2016 | |
| INVENTOR(S) | : Ouali et al. | |

It is certified that error appears in the above-identified patent and that said Letters Patent is hereby corrected as shown below:

On the Title Page

Item (72) Inventors, after "Lahoussine Ouali," delete "Vetraz-Monthhoux" and insert -- Vetraz-Monthoux --.

In the Claims

Column 15:
Line 12 (Claim 9, Line 2), after "80", delete "my" and insert -- mv --.
Line 50 (Claim 15, Line 3), after "80", delete "my" and insert -- mv --.

Column 16:
Line 27 (Claim 16, Line 27), after "80", delete "my" and insert -- mv --.

Signed and Sealed this
Third Day of January, 2017

Michelle K. Lee
*Director of the United States Patent and Trademark Office*